US00PP13110P2

(12) United States Plant Patent
Kumar et al.

(10) Patent No.: US PP13,110 P2
(45) Date of Patent: Oct. 22, 2002

(54) ***LIPPIA ALBA* PLANT NAMED 'BHURAKSHAK'**

(75) Inventors: Sushil Kumar; Janak Raj Bahl; Ravi Prakash Bansal; Shri Niwas Garg; Arif Ali Naqvi; Suman Preet Singh Khanuja; Ajit Kumar Shasany; Mahendra Pandurang Darokar; Vikram Singh; Sweta Sinha, all of Uttar Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/538,341

(22) Filed: Mar. 29, 2000

(51) Int. Cl.[7] ..... A01H 5/00

(52) U.S. Cl. ..... Plt./258

(58) Field of Search ..... Plt./258

(56) References Cited

PUBLICATIONS

Linalool rich *Lippia alba* var. Kavach, Kumar, et al Journal of Medicinal and Aromatic Plant Sciences 21 (1999) 1094–1095.

*Primary Examiner*—Bruce R. Campell
*Assistant Examiner*—Susan B. McCormick
(74) *Attorney, Agent, or Firm*—Ladas & Parry

(57) ABSTRACT

A new and distinct mutant plant of *Lippia alba* called 'Bhurakshak,' characterized by novel aroma of the oil constituting 7.2% 1, 8 cineole, 42.3% linalool, 12.9% citral (b) and 14.2% citral (a) as a major terpenoids, and having a unique RAPD profile as shown in FIG. 1 of the drawings.

2 Drawing Sheets

FIELD OF INVENTION

The invention relates to a new and distinct mutant plant of *Lippia alba* named 'Bhurakshak' characterized by its aroma has been developed. The plant possesses a novel aroma combining linalool, citral a and citral b as the major constituents in its oil.

BACKGROUND OF THE INVENTION

The present invention relates to a new and distinct chemotype of *Lippia alba*, a member of the family Verbenaceae. The genus Lippia is known to consist of about 200 species of herbs, shrubs and small trees, widely distributed in tropical to semi-temperate areas of America, Africa and Asia. Materials in various forms and essential oils of Lippia species have been used in the traditional medicine and control of pest infestations in food grains. Specific strains are recognized as resources of several commercially important terpenoid compounds.

Certain *Lippia alba* wild populations and their cultivated clones have been reported to yield essential oils rich in linalool or terpenoids such as citral and cineole closely related to linalool (Terblanche and Kornelius, 1996. J. Essent. Oil. Res., 8: 471–485). A new chemotype is developed through mutation breeding which has all the four constituents in appreciable amounts to give a novel aroma, which can find wider usage in the cosmetic and soap industry.

SUMMARY OF THE INVENTION

The present invention provides a new and distinct mutant plant of *Lippia alba* called 'Bhurakshak', characterized by novel aroma of the oil constituting 7.2% 1,8 cineole, 42.3% linalool, 12.9% citral (b) and 14.2% citral (a) as a major terpenoids, and having a unique RAPD profile as shown in FIG. 1 of the drawings.

DETAILED DESCRIPTION

The new chemotype of *Lippia alba* named 'Bhurakshak' has been developed through a planned mutation breeding program conducted at Central Institute of Medicinal and Aromatic Plants, Lucknow with an aim to create genotypes with novel aroma suitable for cosmetic and soap industry. For this purpose, a spreading shrub variety 'Kavach' of *Lippia alba* which can be grown on waste land, ravines and slopes to check soil erosion, was selected for mutation breeding. A total of 17,700 single nodal stem cuttings were y-irradiated with different doses (1 kR to 5 kR) during July, 1999. Out of the 3641 surviving plants, 1360 were visually selected after smelling and hydrodistilled in clevenger's apparatus during October 1999.

A plant with number CIMAP/L-640 possessing a novel aroma has been identified with 1,8 cineole (9.6%), linalool (41.7%), citral b (13.5%), and citral a (15.3%) in its essential oil as the major terpenoids. The GC on oil sample was performed using varian gas chromatograph model CX-3400 under the following conditions carrier gas hydrogen, injector and detector temperatures 220° and 225° C., respectively; capillary column (supelcovax-10, 30 m×0.3 mm, film thickness 0.20 $\mu$m); and oven temperature programmed from 80–150° C. @ 5° C./min., then 215° C. @ 7° C./min. The area percentage were obtained on Varian 4400 integrator. This selected plant was multiplied through stem cuttings during the first week of November, 1999. Out of the 14 plants, five randomly selected plants were hydrodistilled in the first week of February 2000 and analyzed for its oil constituents on Gas Chromatograph following similar conditions of GLC. The percentage of major terpenoids in the essential oil were similar to that of the parent mutant plant having 1,8 cineole 7.2%, linalool 42.3%, citral a 14.2% and citral b 12.9% confirming its true breeding behavior.

EVIDENCE OF UNIFORMITY AND STABILITY

The mutant genotype L-640 has remained stable and uniform for its morphological characters and showed consistency in performance for its oil quality attributes during its evaluation and vegetative multiplication.

TYPE AND FREQUENCY OF VARIANTS DURING REPRODUCTION AND MULTIPLICATION

No variant had been found among the progeny during multiplication through vegetative multiplication.

BRIEF DESCRIPTION OF DRAWINGS

FIG. 1 shows a RAPD profile of 'Bhurakshak.'

FIG. 2 shows a close up of the flowering shoot of 'Bhurakshak.'

STATEMENT OF DISTINCTION

The genotype CIMAP/L-640 ('Bhurakshak') possesses a unique novel aroma combining 1,8 cineole (7.2%), linalool (42.3%), citral a (14.2%) and citral b (12.9%) altogether. No other *Lippia alba* genotype has been reported to possess these terpenoids in this proportion to give a special novel aroma. A typical RAPD profile of 'Bhurakshak' generated by 13 primers whose decamer sequences are given in FIG. 1 was generated, which clearly distinguished the genotype from existing accessions of *Lippia alba* was established and is given in FIG. 1.

OBJECTIVE DESCRIPTION OF THE MUTANT CLONE L-640 ('BHURAKSHAK')

1. Genus: Lippia.
2. Species: *Alba.*
3. Family: Verbenaceae.
4. Plant height (cm): 70–80.
5. Growth: Spreading shrub, much branched.
6. Stem: Hard, brownish green.
7. Stem diameter (cm) (at 5th–6th node): 0.8.
8. Leaf: Ovate-oblong or elliptic-oblong, leaf tip acute, margin finely serrate, base truncate, softly strigose, olderleaves dark green and younger ones light or pale green, size: length 3–10 cm and width 2–5 cm. (FIG. 2).
9. Leaf/stem ratio: 0.38.
10. Inflorescence: Flower sessile arranged in axillary dense capitate spikes, corolla light purple, pink or violetish with yellow throat.
11. Fruits: Globose, dry, splitting into two 1-seeded pyrenes.
12. Oil content in the fresh herbage (%): 0.14.
13. Active constituents in the essential oil (%):
    *1,8 cineole.*—7.2.
    *Linalool.*—42.3.
    *Terpinen-4-ol.*—1.1.
    *Citral b* (*neral*).—12.9.
    *Citral a* (*geranial*).—14.2.
    *Geranyl acetate.*—1.9.
    *Geraniol.*—1.0.
14. Seed length (mm): 1.9.
15. Seed width (mm): 1.0.
16. Seed color: Green group (137B).
17. Length of flower (cm): 1.43.
18. Diameter of flower: 0.73.
19. No. of leaves/branches: 28.
20. No. of branches/plant: 2.
21. Leaf texture: Rough.
22. Arrangement of leaves: Opposite.
23. Length of branches and stem (cm): 142.3.
24. Internode length (cm): 10.2.
25. Stem:
    *a. Texture.*—Rough.
    *b. Diameter* (*cm*).—0.8.
26. Petiole length (cm): 0.68.
27. Color of upper surface of leaf: Green group (137C).
28. Color of lower surface of leaf: Green group (138B).

All references to color herein refer to The Royal Horticultural Society Chart. The green foliage, i.e., the leaves and the stem, of the plant are used to obtain the essential oil. Cuttings of the plant establish in soil within a week.

ADDITIONAL DESCRIPTION OF THE STRAIN

The mutant clone possesses a novel aroma with oil constituents which are intermediate between the two other accessions in collection.

TABLE 1

Major terpenoids in the essential oil of available accessions including parent plant and the mutant clone.

| Sl. No. | Active constituents in the oil | LAC-1 | LAC-2 Parent clone | New mutant Clone L-640 |
|---|---|---|---|---|
| 1. | 1,8 Cineole | 0.5 | 5.0 | 7.2 |
| 2. | Linalool | 1.3 | 64.9 | 42.3 |
| 3. | Terpinen-4-ol | 1.1 | 2.5 | 1.1 |
| 4. | Citral b (neral) | 20.3 | 1.7 | 12.9 |
| 5. | Citral a (geranial) | 28.2 | 2.0 | 14.2 |
| 6. | Geranyl acetate | 0.3 | 0.6 | 1.9 |
| 7. | Geraniol | 1.8 | 3.7 | 1.0 |

The mutant genotype CIMAP/L-640 ('Bhurakshak') was bred at the Central Institute of Medicinal and Aromatic Plants (CUVIAP), Lucknow, India under the genetic improvement program on Lippia. The mutant genotype was bred from a parent plant christened 'Kavach'. The parent plant Kavach was released by Central Institute of Medicinal and Aromatic Plants (CIMAP), Lucknow, India and is now in the public domain. The plant material of 'Kavach' (parent plant) is also made available to the public through National Gene Bank of CIMAP. CIMAP is a non-profit Governmental Organization having the facility for multiplying the plant material and there is no restriction to the access and supply of the plant material of the parent plant. The parent plant Kavach is not patented.

The distinct mutant plant of *Lippia Alba* named "Bhurakshak" is planted during the month of July when the maximum temperature remains between 35–42° C. under hot and sunny conditions and the minimum temperature between 27–32° C. The cuttings after gamma-rays treatment are planted immediately and the cuttings establish in the soil within a week by the growth of roots and the plants grow thereafter. The plants are grown by asexual reproduction through stem cutting, in the farm of Central Institute of Medicinal and Aromatic Plants (CIMAP), Lucknow, India.

Bhurakshak has the following botanical characteristics:

a) Flowers: Bracteate, sessile, complete, zygomorphic, pentamorous, hypogynous and cyclio.
b) Calyx: Five sepals and gamosepalous.
c) Corolla: Five petals, gamopetalous, bilipped(4/1), coronary outgrowth present at the throat of corolla.
d) Androecium: Four stamens, didynamous, epipetalous, polyandrous, dorsifixed situated at the throat of corolla and discrete.
e) Gynoccium: Bicarpellary, syncarpous, ovary superior, bilocular with one ovule in each locule, axile placenta, terminal style and capitate stigma.

SEQUENCE LISTING

<160> NUMBER OF SEQ ID NOS: 13

<210> SEQ ID NO 1
<211> LENGTH: 10
<212> TYPE: DNA
<213> ORGANISM: Artificial Sequence
<220> FEATURE:
<223> OTHER INFORMATION: primer for generating random amplified
polymorphic DNA profile of claimed plant

<400> SEQUENCE: 1 aaatcggagc 10

<210> SEQ ID NO 2
<211> LENGTH: 10
<212> TYPE: DNA
<213> ORGANISM: Artificial Sequence
<220> FEATURE:
<223> OTHER INFORMATION: primer for generating random amplified
polymorphic DNA profile of claimed plant

<400> SEQUENCE: 2 tgcgcgatcg 10

<210> SEQ ID NO 3
<211> LENGTH: 10
<212> TYPE: DNA
<213> ORGANISM: Artificial Sequence
<220> FEATURE:
<223> OTHER INFORMATION: primer for generating random amplified
polymorphic DNA profile of claimed plant

<400> SEQUENCE: 3 aacgtacgcg 10

<210> SEQ ID NO 4
<211> LENGTH: 10
<212> TYPE: DNA
<213> ORGANISM: Artificial Sequence
<220> FEATURE:
<223> OTHER INFORMATION: primer for generating random amplified
polymorphic DNA profile of claimed plant

<400> SEQUENCE: 4 gcacgccgga 10

<210> SEQ ID NO 5
<211> LENGTH: 10
<212> TYPE: DNA
<213> ORGANISM: Artificial Sequence
<220> FEATURE:
<223> OTHER INFORMATION: primer for generating random amplified
polymorphic DNA profile of claimed plant

<400> SEQUENCE: 5 cgggatccgc 10

<210> SEQ ID NO 6
<211> LENGTH: 10
<212> TYPE: DNA
<213> ORGANISM: Artificial Sequence
<220> FEATURE:
<223> OTHER INFORMATION: primer for generating random amplified
polymorphic DNA profile of claimed plant -continued

<400> SEQUENCE: 6 gcgaattccg 10

<210> SEQ ID NO 7
<211> LENGTH: 10
<212> TYPE: DNA
<213> ORGANISM: Artificial Sequence
<220> FEATURE:
<223> OTHER INFORMATION: primer for generating random amplified
polymorphic DNA profile of claimed plant

<400> SEQUENCE: 7 ccctgcaggc 10

<210> SEQ ID NO 8
<211> LENGTH: 10
<212> TYPE: DNA
<213> ORGANISM: Artificial Sequence
<220> FEATURE:
<223> OTHER INFORMATION: primer for generating random amplified
polymorphic DNA profile of claimed plant

<400> SEQUENCE: 8 ccaagcttgc 10

<210> SEQ ID NO 9
<211> LENGTH: 10
<212> TYPE: DNA
<213> ORGANISM: Artificial Sequence
<220> FEATURE:
<223> OTHER INFORMATION: primer for generating random amplified
polymorphic DNA profile of claimed plant

<400> SEQUENCE: 9 aagatagcgg 10

<210> SEQ ID NO 10
<211> LENGTH: 10
<212> TYPE: DNA
<213> ORGANISM: Artificial Sequence
<220> FEATURE:
<223> OTHER INFORMATION: primer for generating random amplified
polymorphic DNA profile of claimed plant

<400> SEQUENCE: 10 ggatctgaac 10

<210> SEQ ID NO 11
<211> LENGTH: 10
<212> TYPE: DNA
<213> ORGANISM: Artificial Sequence
<220> FEATURE:
<223> OTHER INFORMATION: primer for generating random amplified
polymorphic DNA profile of claimed plant

<400> SEQUENCE: 11 ttgtctcagg 10

<210> SEQ ID NO 12
<211> LENGTH: 10
<212> TYPE: DNA
<213> ORGANISM: Artificial Sequence
<220> FEATURE:
<223> OTHER INFORMATION: primer for generating random amplified
polymorphic DNA profile of claimed plant -continued

```
<400> SEQUENCE: 12

ggactccacg                                                          10


<210> SEQ ID NO 13
<211> LENGTH: 10
<212> TYPE: DNA
<213> ORGANISM: Artificial Sequence
<220> FEATURE:
<223> OTHER INFORMATION: primer for generating random amplified
      polymorphic DNA profile of claimed plant

<400> SEQUENCE: 13

agcctgacgc                                                          10
```

We claim:

1. A new and distinct variety of *Lippia alba* plant, substantially as illustrated and described herein.

* * * * *

Figure 1: Typical RAPD Profile of Bhurakshak

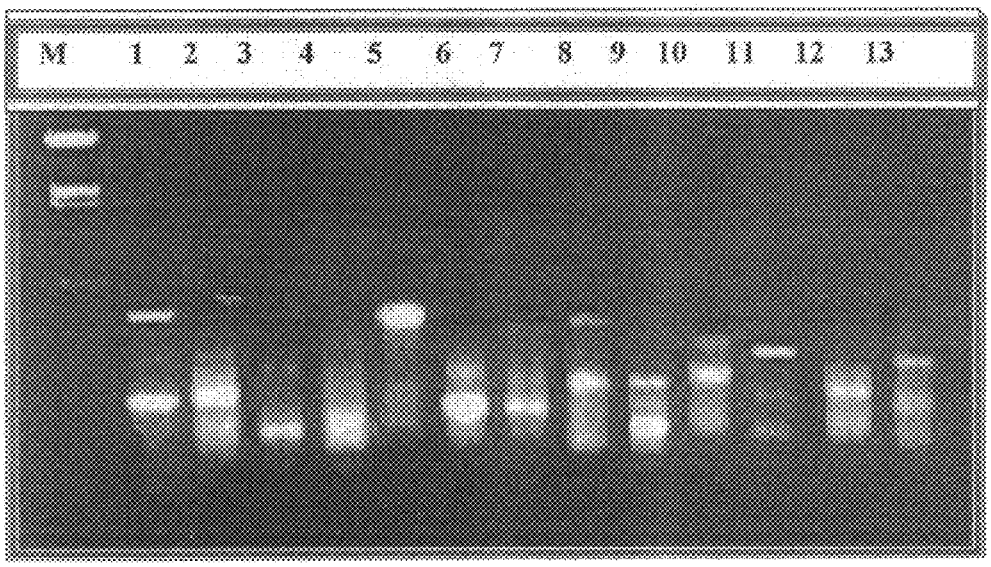

Lane M: DNA Marker λ. Eco RI + Hind III

Lane M: DNA Marker λ Eco RI + Hind III

Lane 1: AAATCGGAGC (SEQ ID NO 1)
Lane 2: TGCGCGATCG (SEQ ID NO 2)
Lane 3: AACGTACGCG (SEQ ID NO 3)
Lane 4: GCACGCCGGA (SEQ ID NO 4)
Lane 5: CGGGATCCGC (SEQ ID NO 5)
Lane 6: GCGAATTCCG (SEQ ID NO 6)
Lane 7: CCCTGCAGGC (SEQ ID NO 7)
Lane 8: CCAAGCTTGC (SEQ ID NO 8)
Lane 9: AAGATAGCGC (SEQ ID NO 9)
Lane 10: GGATCTGAAC (SEQ ID NO 10)
Lane 11: TTGTCTCAGG (SEQ ID NO 11)
Lane 12: GGACTCCACG (SEQ ID NO 12)
Lane 13: AGCCTGACGC (SEQ ID NO 13)